US006787563B2

(12) United States Patent
Jacobelli

(10) Patent No.: US 6,787,563 B2
(45) Date of Patent: Sep. 7, 2004

(54) CRYSTALLINE 3-{4-METHYL-3-[METHYL-(7H-PYRROLO[2,3-D]PYRIMIDIN-4-YL)-AMINO]-PIPERIDIN-1-YL}-3-OXO-PROPIONITRILE CITRATE

(75) Inventor: Henry Jacobelli, Paray-Vieille-Poste (FR)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/319,363

(22) Filed: Dec. 13, 2002

(65) Prior Publication Data

US 2003/0139448 A1 Jul. 24, 2003

(30) Foreign Application Priority Data

Dec. 21, 2001 (FR) .............................. 01 16785

(51) Int. Cl.⁷ ..................... A61K 31/401; C07D 207/06
(52) U.S. Cl. ....................................... 514/408; 548/579
(58) Field of Search ........................ 514/408; 548/579

(56) References Cited

U.S. PATENT DOCUMENTS

| 5,849,760 A | 12/1998 | Calvet et al. ............... 514/320 |
| 6,057,371 A | 5/2000 | Glennon .................... 514/649 |

FOREIGN PATENT DOCUMENTS

| FR | 2760454 | 3/1997 |
| WO | WO9839295 | 9/1998 |
| WO | WO9839296 | 9/1998 |

OTHER PUBLICATIONS

WO98/39295 is the PCT equivalent of FR2760454.
Rajewski, et al. Pharmaceutical Applications of Cyclodextrins, *Journ. of Pharmaceutical Sciences* 85 (11), pp. 1142–1169 (1996).

H.L. DuPont "Review Article: Infectious Diarrhoea", *Allment Pharmacol Ther* 8, pp. 3–13 (1994).
Ciancio, et al. "Endotoxin–Induced Alterations in Rat Colonic water and Electrolyte Transport", *Gastroenterology* 103, pp. 1437–1443 (1992).
Farthing "The Role of Somatostatin Analogues in the Treatment of Refractory Diarrhoea", *Digestion* 57 (1), pp. 107–113 (1996).
Camilleri "Effects of Somatostatin Analogues on Human Gastrointestinal Motility", *Digestion* 57 (1), pp. 90–92 (1996).
Farthing "Chronic Diarrhoea: Current Concepts on Mechanisms and Management", *Eur. Journ of Gastroenterology & Hepatology* 8, pp. 157–167 (1996).
Berge, et al. "Pharmaceutical Salts" *Journ of Pharmaceutical Sciences* 66 (1), pp. 1–19 (1977).

*Primary Examiner*—Patricia L. Morris
(74) *Attorney, Agent, or Firm*—Peter C. Richardson; Gregg C. Benson; Christine S. Lee

(57) ABSTRACT

The present invention relates to substituted N-(cyclopropylmethyl)azacycloalkanes of the following formula (I):

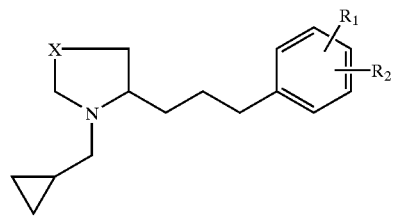

in which, independently, $R_1$ is hydrogen or halogen, $R_2$ is hydrogen or halogen and X is methylene or ethylene, their salts, the pharmaceutical compositions containing them, their use as antidiarrhoeal medicaments and methods for their preparation.

4 Claims, No Drawings

CRYSTALLINE 3-{4-METHYL-3-[METHYL-(7H-PYRROLO[2,3-D]PYRIMIDIN-4-YL)-AMINO]-PIPERIDIN-1-YL}-3-OXO-PROPIONITRILE CITRATE

This application claims priority from French patent application number 0116785 of Dec. 21, 2001.

The invention relates to novel substituted N-(cyclopropylmethyl)azacycloalkanes, their salts, the pharmaceutical compositions containing them, their use as antidiarrhoeal medicaments and methods for their preparation.

The secretory abnormalities of the digestive apparatus are, with motility disorders, responsible for the majority of chronic or acute diarrhoeas which, in 1990, were estimated to be the second cause of mortality worldwide, in particular in infant populations of developing countries.

Chronic diarrhoeas are defined by their persistent duration generally of over two weeks. Their various aetiologies and the action to be taken in this group of pathologies have been documented in particular by M. Cerf, *Gastroenterol. Clin. Biol,* 1992, 16: T 12-T 21. and by M. J. G. Farthing, *Eur. J. of Gastroenterol. & Hepatol.* 1996, 8:157–167.

Acute diarrhoeas, which are, in the great majority, of infectious origin, have also been documented by M. Cerf and M. Hagiage: Diarrhées aiguës d'origine infectieuse [Acute diarrhoeas of infectious origin]. *Éditions Techniques—Encycl. Méd. Chir.* (Paris, France), Gastro-entérologie, 9061 A10, 1992, 20p.; and H. L. Dupont, Review article: Infectious diarrhoea—*Aliment. Pharmacol. Ther.* 1994; 8: 3–13. Among other causes, the important role of toxinogenesis during bacterial infection is acknowledged, and, in particular, the expression of the pathogenicity by the synthesis of cytotoxins and of enterotoxins, which are responsible for secretory diarrhoea with a water-electrolyte component; the representative physiopathological model is that of cholera diarrhoea.

Other infectious agents are known to cause such diarrhoeas, such as Salmonella, *Escherichia coli* and *Clostridium difficile* strains. The latter agents, and more particularly *C. difficile*, are responsible for chronic and abundant secretory diarrhoeas, often of nosocomial origin, in subjects subjected to an intensive antibiotic therapy such as patients who are seropositive for HIV. In the latter, the particularly incapacitating diarrhoeas are often associated with malabsorption, and contribute towards rapidly establishing an alarming state of undernourishment. They can also represent an undesirable effect of the antiviral treatments to which these patients are subjected. In the symptomatic treatment of secretory diarrhoeas, rehydration of the patients is recommended and sometimes proves essential.

Certain compounds (phenothiazine, clonidine, bismuth salts) have proved active in the treatment of secretory diarrhoeas, but their delicate use because of their side effects has led to their widespread use being abandoned.

The usual treatments involve adsorbent compounds (smectite), modulators of the intestinal flora and, very widely, so-called slowing compounds, which are morphinomimetic antidiarrhoeals: loperamide and diphenoxylate; the latter products are agents for slowing digestive tube transit and, for this reason, of disputed if not inadvisable usefulness for certain conditions because of the delay which they bring about in the natural evacuation of pathogenic microorganisms and their toxins.

More recently, it has been proposed to treat these diarrhoeas with acetorphan, a synthetic dipeptide, with antisecretory effect, an enkephalinase inhibitor, and therefore which maintains the effect of enkephalins; the enkephalins, antisecretory endogenous neuropeptides of the intestinal wall, are normally rapidly hydrolysed in vivo by enkephalinases, which makes their effect transient.

As regards the therapy of diarrhoeas in patients infected with HIV, it is frequently necessary to have recourse to cumbersome methods, which can only be performed in a hospital setting, such as rehydration and renourishment by the enteral or parenteral routes, with which a symptomatic antidiarrhoeal treatment and an antibiotic therapy directed against the possible pathogenic agent are combined. The usual antidiarrhoeals most often have only a relative and episodic efficacy. Recently, for these diarrhoeas and more generally for the cases refractory to conventional therapies, peptides inhibiting gastrointestinal motility and secretion, related to somatostatin have been proposed (M. Camilleri, *Digestion* 1996; 57 suppl. 1:90–92, and M. J. G. Farthing, *Digestion* 1996; 57 suppl. 1:107–113). Synthetic compounds which are substitutes for this endogenous mediator are octreotide and valtreotide, both octapeptides proposed with some success for the treatment of secretory diarrhoeas of AIDS. Although their duration of action is considerably longer than that of somatostatin, these expensive compounds are only active through repeated administration by the parenteral route, which leads to prohibitive treatment costs and makes their use practically impossible in an outpatient department. Furthermore, their lack of specificity can cause side effects which dramatically aggravate the state of undernourishment of the patients (disorders in the regulation of the metabolism of carbohydrates and an increase in steatorrhoea).

International Application WO 95/15948 describes 2-(arylalkenyl)azacycloalkane derivatives, their method of preparation and their therapeutic application. These compounds are proposed for the preparation of antipsychotic medicaments and are useful in gastroenterology. Racemic (E)-2-(3,4-dichlorocinnamyl)-1-cyclopropylmethylpiperidine and its hydrochloride are described in Example 2E and, moreover, it is stated therein that the compounds of the application are active on secretory diarrhoeas induced in mice by the salmonella lipopolysaccharide (LPS), which suggests their usefulness in the treatment of secretory diarrhoeas of diverse aetiologies.

In International Application WO 98/39296 (S)-1-cyclopropylmethyl-2-[(E)-3-(3,4-dichlorophenyl)allyl] piperidine, its addition salts and their use in the preparation of pharmaceutical compositions intended for the treatment of diarrhoeas are described.

The present invention now provides novel compounds for the treatment of gastrointestinal disorders, in particular diarrhoeas. The invention thus relates to N-(cyclopropylmethyl)azacycloalkanes of the following general formula I:

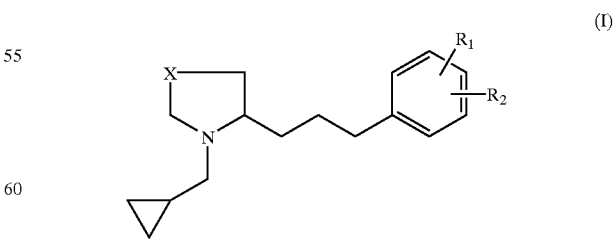

(I)

in which $R_1$ is hydrogen or halogen, $R_2$ is hydrogen or halogen and X is methylene or ethylene.

In the present description the expression halogen is understood to mean fluorine, chlorine, bromine and iodine.

The present invention includes the individual enantiomers of the compounds having formula I and mixtures thereof. Separation of the racemate into the enantiomers can be carried out by methods known in the art.

Among the particularly preferred compounds of the present invention are the following compounds:

1-cyclopropylmethyl-2-(3-phenylpropyl)pyrrolidine;
(2R)-1-cyclopropylmethyl-2-(3-phenylpropyl)pyrrolidine;
1-cyclopropylmethyl-2-(3-phenylpropyl)piperidine, and
(2R)-1-cyclopropylmethyl-2-[3-(3,4-dichlorophenyl) propyl]piperidine.

The invention also relates to a pharmaceutical composition comprising at least one compound of general formula (I) as defined above, in combination with a pharmaceutically acceptable carrier.

The invention also relates to the use of an N-(cyclopropylmethyl)azacycloalkane of general formula (I) as a medicament.

The invention also relates to the use of an N-(cyclopropylmethyl)azacycloalkane of general formula (I) for the preparation of a medicament intended for the prevention and treatment of gastrointestinal conditions, particularly diarrhoeas in mammals, in particularly humans.

The invention thus provides a method for treating a patient suffering from a gastrointestinal condition, in particular diarrhoea, by administering a therapeutically effective amount of an N-(cyclopropylmethyl)azacycloalkane of general formula (I).

Among the diarrhoeas requiring a treatment according to the invention are those observed during irritable bowel syndrome (IBS), a particularly frequent digestive functional disorder.

The compounds used in the invention include the pharmaceutically acceptable solvates, hydrates and salts, and the polymorphs (different crystalline structures), of the compounds of formula I.

The pharmaceutically acceptable salts include for example: acetate, benzenesulphonate, benzoate, bicarbonate, bitartrate, bromide, calcium acetate, camsylate, carbonate, chloride, citrate, dihydrochloride, edetate, edisylate, estolate, esylate, fumarate, gluceptate, gluconate, glutamate, glycoloylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methyl nitrate, methyl sulphate, mucate, napsylate, nitrate, pamoate (embonate), pantothenate, phosphate/diphosphate, polygalacturonate, salicylate, stearate, subacetate, succinate, sulphate, tannate, tartrate, theoclate, triethiodide, benzathine, chloroprocaine, choline, diethanolamine, ethylenediamine, meglumine, procaine, aluminium, calcium, lithium, magnesium, potassium, sodium, and zinc (see also *Pharmaceutical salts* de Berge S. M. et al. (1997) J. Pharm. Sci. 66:1–19, the content of which is incorporated by way of reference).

The use of a prodrug of a compound according to the invention is also envisaged. (See in particular Bundgaard, et al., (1987) Acta Pharm. Suec. 24:233–246).

Mixtures of compounds are also envisaged.

The compounds of the invention are administered in the form of compositions which are appropriate to the nature and importance of the condition to be prevented or treated. The daily dosage in humans is usually between 0.1 mg and 0.5 g of product which may be absorbed in one or more doses. The compositions are prepared by common methods for persons skilled in the art and generally comprise 0.1 to 60% by weight of active ingredient (compound of formula I) and 40 to 99.9% by weight of appropriate pharmaceutical vehicle. The compositions of the present invention are therefore prepared in forms compatible with the desired route of administration. By way of example, the following pharmaceutical dosage forms may be envisaged:

1) Forms for Oral Administration:

Tablets, cachets, sachets of powder for oral suspension, gelatin capsules, gastro-resistant gelatin capsules, prolonged release forms, emulsions, capsules or HPMR gelatin capsules, lyophilysates to be melted under the tongue, oral solutions; suspensions and sachets of powder for oral solution.

The powders, tablets, cachets or encapsulated forms preferably contain from 1% to 70% of the active ingredient. Appropriate carriers are, for example, magnesium carbonate, magnesium stearate, talc, lactose, sugar, pectin, dextrin, starch, gum tragacanth, methyl cellulose, sodium carboxymethyl cellulose, low melting wax, cocoa butter and the like.

The tablets, powders, cachets and capsules may be used as a unit dose for administration by the oral route.

In the powders, the carrier is a finely divided solid which is in the form of a mixture with the compound of general formula I which is finely divided.

In the tablets, the active compound is mixed with the carrier having the required binding properties in an appropriate quantity, and then the mixture is tableted in the required form and size.

The aqueous solutions for oral administration may be prepared by dissolving the active ingredient and adding, if necessary, colourings, taste-enhancing agents, flavourings, stabilizers, thickening agents, and the like. By way of example, the active ingredient may be dispersed in the form of a finely divided powder in water with a viscous material such as synthetic gums, resins, methyl cellulose, sodium carboxymethyl cellulose, and other suspending agents known in the galenic art.

2) Forms for Rectal Administration:

There may be mentioned, inter alia, enemas, suppositories and gels. For the preparation of suppositories, a low melting point wax, such as a mixture of fatty acid glycerides and cocoa butter is in a first instance melted, and then the active ingredient is dispersed therein, for example with mechanical stirring. The molten homogenous mixture is then poured into moulds of appropriate shape and then allowed to cool and solidify.

3) Forms for Parenteral Administration:

Intravenous Route:

Aqueous solutions, water/cosolvent solutions, solutions using one or more solubilizers, colloidal suspensions, emulsions, nanoparticulate suspensions which can be used for the injection of prolonged release forms, dispersed forms and liposomes.

Sterile water and/or propylene glycol solutions of the active ingredient may be mentioned as examples of liquid preparations appropriate for administration by the parenteral route. The liquid preparations may also be formulated in the form of aqueous solutions of polyethylene glycol.

Subcutaneous/Intramuscular Route:

In addition to the forms which can be used by the intravenous route which can also be used for the subcutaneous and intramuscular routes, other types of form such as suspensions, dispersed forms, prolonged release gels and prolonged release implants may also be used.

4) Forms for Topical Administration:

Among the most common topical forms are creams, gels (aqueous phases gelled with polymers), patches, which are dressings to be put directly on the skin, sprays, emulsions and solutions.

5) Forms for Pulmonary Administration:

This category includes forms such as solutions for aerosols, powders for inhalers, and other appropriate forms.

6) Forms for Nasal Administration:

Included here are in particular solutions for drops.

It is also possible to envisage the use of forms allowing the administration of ophthalmic solutions or allowing the administration of the active ingredient by the vaginal route.

Another important category of pharmaceutical dosage form which may be used in the context of the present invention relates to the forms which make it possible to improve the solubility of the active ingredient. By way of example, the use of aqueous solutions of cyclodextrin, and more particularly of the forms comprising hydroxypropyl-beta-cyclodextrin, may be envisaged. A detailed review of this type of pharmaceutical dosage form is presented in the article which appeared under the reference *Journal of Pharmaceutical Sciences*, 1142–1169, 85 (11), 1996, and incorporated by way of reference into the present application. The use of a prodrug of a compound according to the invention is also envisaged. (See in particular Bundgaard, et al., *Acta Pharm. Suec.*, 1987; 24:233–246).

The compounds of the invention possess antidiarrhoeal properties.

The invention also relates to a method for preparing the compounds according to the invention, as illustrated in the reaction scheme below. The starting products are commercially available or may be synthesized by conventional methods.

Synthesis Scheme

In the description which follows, the synthesis is described in a general manner, and then exemplified with reference to the compounds of Examples 1 to 4. It is however clear that this method applies in the same manner to the other compounds of formula (I), the starting materials being appropriately chosen.

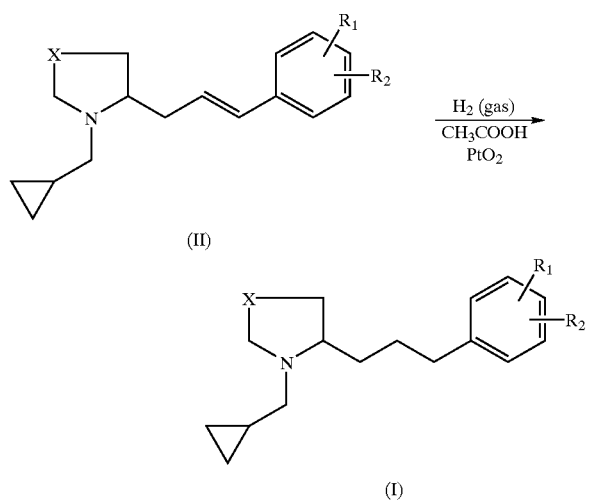

The products (II) are prepared as described in the documents WO 95/15948 or WO 98/39296.

In general, the saturation of the double bond may be obtained by catalytic hydrogenation using an appropriate catalyst and an appropriate solvent.

Typically, the heterogeneous catalysts used are Raney nickel, palladium on carbon, platinum oxide, rhodium oxide.

The solvents generally used during this reaction are methanol, ethanol, dioxane, dimethylformamide and acetic acid.

Preferably, as in the examples described below, $PtO_2$ in acetic acid at room temperature at a hydrogen pressure in the region of 5 bar is used.

EXAMPLES

Example No. 1

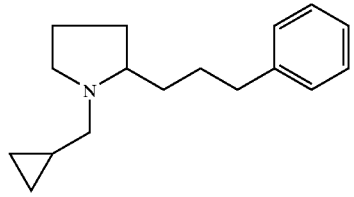

1-Cyclopropylmethyl-2-(3-phenylpropyl)pyrrolidine 1.0 g (4.14 mmol) of 1-cyclopropylmethyl-2-(3-phenylallyl)pyrrolidine—prepared as described in International Application WO 95/15948—and 50 ml of pure acetic acid are introduced into a stainless steel autoclave. 21 Mg of $PtO_2$ are added to this solution.

The reactor is hermetically closed, purged three times under vacuum and under nitrogen and then three times under vacuum and under hydrogen, and then placed under a hydrogen pressure of 5 bar and under stirring.

After about 4.25 h, the hydrogenation is complete. The reactor is purged under vacuum and then under nitrogen, and the reaction mixture filtered on infusorial earth in order to remove the catalyst.

After concentration under vacuum, the residue obtained is solubilized in 100 ml of ether and then extracted with 1×50 ml of 0.1 N HCl and 2×25 ml of $H_2O$.

The acidic aqueous phase is alcalinized in the presence of ice at pH 12 with concentrated sodium hydroxide, and extracted with 3×50 ml of ether. After washing with a saturated NaCl solution and drying over $Na_2SO_4$, the organic phase is concentrated to dryness in a rotary evaporator.

1 g of product is obtained, that is a crude yield in the region of 100%.

The corresponding hydrochloride is prepared by dissolution in 15 ml of dichloromethane and addition of 1.7 ml of about 5 N hydrochloric ether. After concentrating under vacuum, the residue is crystallized from an isopropanol/ether mixture. The precipitate is filtered, washed and dried under vacuum.

| Weight = 0.8 g | Yield = 69% |
| --- | --- |

TLC ($CH_2Cl_2$/MeOH containing 10% $NH_4OH$ 95/5): Rf=0.70 m.p.=113° C.

NMR: $CDCl_3$ $^1H$ δ (ppm) base 0.1 (m, 2H); 0.5 (m, 2H); 0.85 (m, 1H); 1.-2.0 (m, 9H); 2.1 (q, 2H); 2.7 (m, 3H); 3.3 (t, 1H); 7.2 (m, 5H).

IR: 2951, 2547, 2504, 1739, 1463, 1435, 1354, 1217, 1052, 1024, 926, 756, 700 $cm^{-1}$ $C_{17}H_{26}ClN$

| Calculated | C = 72.96 | H = 9.36 | Cl = 12.67 | N = 5.01 |
| Found | C = 73.05 | H = 9.44 | Cl = 12.77 | N = 4.95 |

Example No. 2

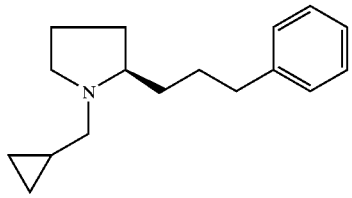

(R)-1-Cyclopropylmethyl-2-(3-phenylpropyl) pyrrolidine 1.5 g (4.14 mmol) of (S)-1-cyclopropylmethyl-2-(3-phenylallyl)pyrrolidine—prepared as described in International Application WO 95/15948—and 65 ml of pure acetic acid are introduced into a stainless steel autoclave. 28 mg of $PtO_2$ are added to this solution.

The reactor is hermetically closed, purged three times under vacuum and under nitrogen and then three times under vacuum and under hydrogen. After an identical treatment to that described in the preceding example, 1.2 g of an oily residue are obtained, purified by flash chromatography on silica using a dichloromethane gradient which is progressively enriched with methanol containing 10% $NH_4OH$. 0.7 g of an oily residue is obtained.

The hydrochloride is prepared as above and crystallized from an isopropanol/ether mixture.

| Weight = 0.55 g | Yield = 36% |

TLC: $CH_2Cl_2$/MeOH (containing 10% $NH_4OH$ 97/3): Rf=0.15 m.p.=143.7° C.

Alpha D: (base 4% in MeOH)=−88.4°

Chiral HPLC>95%

NMR: $CDCl_3$ $^1H$ δ (ppm) HCl 0.2–0.5 (m, 2H); 0.65–0.80 (m, 2H); 1.1–1.4 (m, 1H); 15–3.35 (m, 14H); 3.8–4.05 (m, 1H); 7.0–7.35 (m, 5H); 12.1 (bs, 1H)

IR: 2943, 2546, 2505, 2361, 1467, 1431, 1048, 923, 833, 756, 702 cm$^{-1}$ $C_{17}H_{26}ClN$

| Calculated | C = 72.96 | H = 9.36 | Cl = 12.67 | N = 5.01 |
| Found | C = 73.05 | H = 9.37 | Cl = 12.67 | N = 5.02 |

Example No. 3

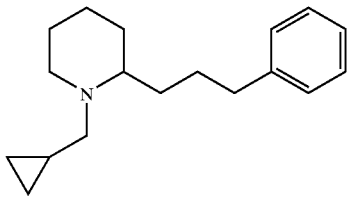

1-Cyclopropylmethyl-2-(3-phenylpropyl)piperidine 1.5 g (5.14 mmol) of 1-cyclopropylmethyl-2-(3-phenylallyl)pyrrolidine—prepared as described in International Application WO 95/15948—and 62 ml of pure acetic acid are introduced into a stainless steel autoclave. 27 mg of $PtO_2$ are added to this solution.

The reactor is hermetically closed, purged three times under vacuum and under nitrogen and then three time under vacuum and under hydrogen.

Using the same treatments and purifications as above, an oily product in the form of a base is obtained.

| Weight = 0.65 g | Yield = 49% |

HPLC purity=98.3%

TLC ($CH_2Cl_2$/MeOH containing 10% $NH_4OH$ 97/3): Rf=0.15

NMR: $CDCl_3$ $^1H$ δ (ppm) base

0–0.2 (m, 2H); 0.35–0.50 (m, 2H); 0.7–0.9 (m, 1H); 1.05–1.75 (m, 10H); 2.1–2.35 (m, 3H); 2.35–2.7 (m, 3H); 2.95–3.10 (m, 1H); 7.0–7.3 (m, 5H);

IR: 2931, 2846, 1495, 1451, 1330, 1133, 1085, 1017, 823, 746 cm$^{-1}$ $C_{18}H_{27}N$

| Calculated | C = 83.99 | H = 10.57 | N = 5.44 |
| Found | C = 83.38 | H = 10.57 | N = 5.57 |

Example No. 4

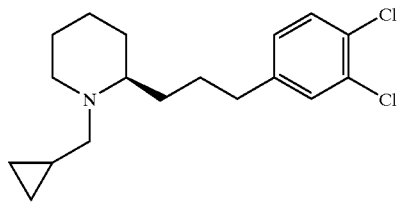

(2R)-1-Cyclopropylmethyl-2-[3-(3,4-dichlorophenyl)propyl]piperidine 3.0 g (8.3 mmol) of (2S)-1-cyclopropylmethyl-2-[3-(3,4-dichlorophenyl)allyl]piperidine—prepared as described in International Application WO 98/39296—and 100 ml of pure acetic acid are introduced into a stainless steel autoclave. 45 mg of $PtO_2$ are added to this solution.

The reactor is hermetically closed, purged three times under vacuum and under nitrogen and then three times under vacuum and under hydrogen. Using the same protocols and purifications as above, an oily product in the form of a base is obtained.

| Weight = 1.2 g | Yield = 44% |
|---|---|

HPLC purity=97.15%
TLC: (CH$_2$Cl$_2$/MeOH containing 10% NH$_4$OH 97/3): Rf=0.15
Alpha D=−42.2° (c=5.7%, MeOH)
NMR: CDCl$_3$ $^1$H δ (ppm) base
0–0.15 (m, 2H); 0.4–0.60 (m, 2H); 0.7–0.9 (m, 1H); 1.2–1.80 (m, 10H); 2.1–2.35 (m, 3H); 2.4–2.65 (m, 3H); 3.0–3.15 (m, 1H); 7.0 (d, 1H); 7.25 (s, 1H); 7.3–7.40 (d, 1H)
IR: 2932, 2862, 1556, 1473, 1395, 1334, 1258, 1131, 1030, 831, 819 cm$^{-1}$ $^C_{18}$H$_{25}$ Cl$_2$N

| Calculated | C = 66.26 | H = 7.72 | Cl = 21.73 | N = 4.29 |
|---|---|---|---|---|
| Found | C = 66.09 | H = 7.74 | Cl = 21.71 | N = 4.29 |

Example 5

Inhibition of Experimental Toxigenic Diarrhoeas a) Diarrhoea Induced by Salmonella Lipopolysaccharide (LPS)

The test is performed on mice according to a procedure based on M. J. Cancio et al. (Gastroenterology November 1992, 103 (5), 1437–43) which, in rats, induces impairments in the transport of water and electrolytes in the colon by an endotoxin.

Procedure: male dBA2 mice (Iffa-credo, les Oncins, France) having a weight of between 20 and 25 g are placed in individual cages. After adaptation of the animals to their environment, the test product is administered by the oral route in aqueous solution or suspension, and then one hour later (to of the trial), an injection of Salmonella enteriditis lipopolysaccharide (LPS) (Sigma product—ref. L6761) is made in the vein of the tail at the rate of 15 mg/kg. A preweighed filter paper is then placed under each cage and the weight of faeces eliminated by the animals in two hours (t$_{120}$) is determined. The effect of the test product is determined and is expressed as a percentage inhibition of the weight of faeces at the dose considered relative to the weight of faeces of a control group of animals which received under the same conditions only LPS. These results make it possible to calculate the ED$_{50}$ of the compounds, which is the effective dose allowing 50% inhibition of the weight of the faeces caused by the adminstration of the diarrhoeal agent.

Under these conditions, the product of Example 1 is found to be very active, with an ED$_{50}$ by the oral route of 0.0047 μg/kg.

b) Diarrhoea Induced by the *Escherichia Coli* Heat-Stable Toxin

Fed male NMRI mice (30–35 g) are weighed and placed in individual cages previously lined with white paper allowing visualization of the faecal materials discharged. The faeces are recovered as soon as they are discharged and grouped together by periods of 30 min, for 120 min. The faeces thus grouped together are weighed before (fresh weight) and after (dry weight) drying at 120° C. for 24 h. The quantity of water present in the faeces is calculated as the difference (fresh weight−dry weight).

The *Escherichia coli* heat-stable toxin (Sigma, E5763) is administered by the oral route at time zero at the dose of 600 U/mouse. The animals of the control group receive, at time zero, an oral administration of physiological saline. The test products are administered by the oral route one hour before the administration of the toxins.

The results are expressed as quantity of faecal water accumulated at time 120 min and make it possible to calculate the ED50 of the compounds which is the effective dose allowing 50% inhibition of the weight of water in the faeces under the action of the test product.

c) Diarrhoea Induced by the *Clostridium Difficile* A and B Toxins

The experimental protocol, the calculation and the expression of the results are identical to those described above. The *Clostridium difficile* A and B toxins are administered by the oral route at time zero at the dose of 6 ng/mouse.

Example 6

Inhibition of Intestinal Secretion Induced by the Cholera Toxin So-called Enteropooling Technique Female Wistar rats (160–180 g) are fasted from solid food 24 h before the test. At time zero, the animals receive, by the oral route, 0.1 mg/kg of cholera toxin (Sigma, C3012). Three hours later, the animals are sacrificed by cervical dislocation. After median laparotomy, the intestine is ligated at the level of the pylorus and of the ileocaecal junction. It is then removed (from the duodenum up to the caecum), weighed full, and then empty.

The test products are administered by the oral route one hour before the administration of the cholera toxin. The results are expressed as weight of intestinal content and make it possible to calculate the ED$_{50}$ of the compounds, which is the effective dose allowing 50% inhibition of the weight of the intestinal content under the action of the test product.

What is claimed is:
1. Compound of the following formula (I):

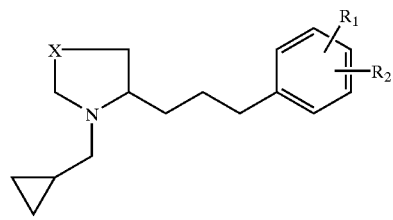

in which, independently, R$_1$ is hydrogen or halogen, R$_2$ is hydrogen or halogen and X is methylene; or a pharmaceutically acceptable salt thereof.

2. Compound according to claim 1, in which R$_1$ and R$_2$ represent the same group.

3. The compound according to claim 1, or a pharmaceutically acceptable salt of the compound selected from the group consisting of:

1-cyclopropylmethyl-2-(3-phenylpropyl)pyrrolidine, and (2R)-1-cyclopropylmethyl-2-(3-phenylpropyl) pyrrolidine.

4. A pharmaceutical composition comprising an effective quantity, prophylactically or therapeutically, of a compound according to any one of claims 1, 2 or 3 and a pharmaceutically acceptable excipient.

* * * * *